United States Patent [19]

Bays et al.

[11] 3,932,416
[45] Jan. 13, 1976

[54] N-TETRAZOLYL QUINALDAMIDES

[75] Inventors: David Edmund Bays; Mervyn Evan Peel; David Martin Waters, all of London, England; Gwynn Pennant Ellis, Cardiff, Wales

[73] Assignee: Allen & Hanburys Limited, London, England

[22] Filed: June 21, 1973

[21] Appl. No.: 372,027

[30] Foreign Application Priority Data
July 3, 1972 United Kingdom............... 30990/72

[52] U.S.................... Cl.260/287 F; 260/247.5 GP; 260/268 BQ; 260/287 L; 424/258
[51] Int. Cl.²........................................ C07D 215/16
[58] Field of Search..................... 260/287 R, 308 R

[56] References Cited
UNITED STATES PATENTS
3,391,146  7/1968  Godfrey.......................... 260/287 R OTHER PUBLICATIONS
Perron et al., J. Med. Chem., Jan. 1966, Vol. 9, p. 141.

Primary Examiner—Donald G. Daus
Assistant Examiner—David E. Wheeler
Attorney, Agent, or Firm—Bacon & Thomas

[57] ABSTRACT

Compounds of the general formula (I):

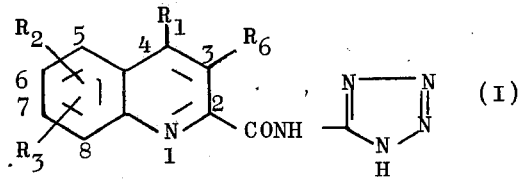

in which $R_1$, $R_2$ and $R_3$ may be the same or different and each represents a hdyrogen atom, an alkyl group, a nitro group, a halogen atom or a group of the formula $-NR_4R_5$ or $-OR_4$; in which the groups $R_4$ and $R_5$ may be the same or different and each represent a hydrogen atom, or an alkyl, alkenyl or cycloalkyl group (which alkyl group may optionally be substituted by alkoxy, hydroxy, amino, alkylamino, dialkylamino or aryl groups) or $R_4$ and $R_5$ together with the nitrogen atom form a heterocyclic ring which may optionally contain additional hetero atoms, e.g. morpholino or piperazinyl; and $R_6$ represents a hydrogen atom or an alkyl group.

These compounds have biological activity, particularly in inhibiting the release of spasmogenic substances arising as a consequence of antigen-antibody reactions.

35 Claims, No Drawings

N-TETRAZOLYL QUINALDAMIDES

This invention relates to novel quinaldic acid derivatives, to processes for the production thereof and to pharmaceutical compositions containing such derivatives.

We have found that certain new quinaldic acid derivatives have useful pharmacological activity and in particular inhibit the release of spasmogenic substances arising as a consequence of antigen-antibody reactions.

Accordingly the present invention provides compounds of the general formula (I):

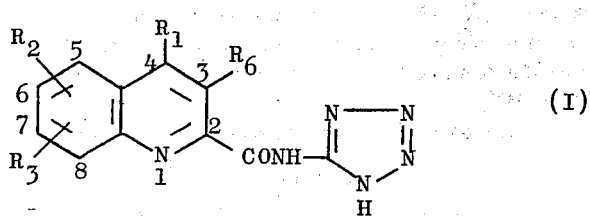

in which $R_1$, $R_2$ and $R_3$ may be the same or different and each represents a hydrogen atom, an alkyl group, a nitro group, a halogen atom or a group of the formula $-NR_4R_5$ or $-OR_4$; in which the groups $R_4$ and $R_5$ may be the same or different and each represent a hydrogen atom, or an alkyl, alkenyl or cycloalkyl group (which alkyl group may optionally be substituted by alkoxy, hydroxy, amino, alkylamino, dialkylamino or aryl groups) or $R_4$ and $R_5$ together with the nitrogen atom form a heterocyclic ring which may optionally contain additional hetero atoms, e.g. morpholino or piperazinyl; and $R_6$ represents a hydrogen atom or an alkyl group. The terms alkyl and alkenyl as used herein, means such groups which are straight or branched chain and contain from 1 to 6 carbon atoms (preferably 1 to 4 carbon atoms) and from 2 to 6 carbon atoms (preferably 2 to 4 carbon atoms) respectively. Cycloalkyl means a carbocyclic ring containing 5 or 6 carbon atoms.

The formulae in the present application depict the 1[H] isomer of the tetrazole ring. Prototropy enables these to be converted into the 2[H] structure and the invention therefore extends also to the 2[H] structure, given below:

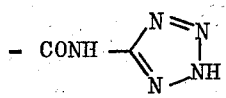

The invention also includes pharmaceutically acceptable salts of the above compounds and esters with simple aliphatic acids (including formic acid).

Preferred salts may be those with alkali metals, e.g. sodium or with organic bases, e.g. dimethylaminoethanol.

Where basic substituents are present the invention also covers salts with inorganic or organic acids.

Preferred meanings for the groups $R_1$, $R_2$ and $R_3$ and $R_6$ are set out below:

$R_1$

Hydrogen, halogen preferably chlorine, hydroxy, alkylamino, preferably ethylamino, hydroxyalkylamino, preferably 2-hydroxyethylamino or 3-hydroxypropylamino, hydroxyalkylalkylamino, preferably 2-(hydroxyethyl)-methylamino, dihydroxyalkylamino, preferably 2,3-dihydroxypropylamino, alkoxyalkylamino, preferably 2-methoxyethylamino, aminoalkylamino, preferably 2-aminoethylamino, dialkylaminoalkylalkylamino, preferably 2-(dimethylaminoethyl)methylamino, cycloalkylamino, preferably cyclohexylamino, morpholino, piperazinyl, N-methyl piperazinyl, alkoxy, preferably methoxy or butoxy, alkenyloxy, preferably allyloxy, aralkyloxy, preferably benzyloxy, hydroxyalkoxy, preferably hydroxyethoxy, acyloxyalkoxy, preferably 2-formyloxyethoxy, alkoxyalkoxy preferably 2-methoxyethoxy.

$R_2$ and $R_3$

Hydrogen, 6-alkoxy preferably 6-methoxy, 6-nitro, 6-amino, 6-alkyl, preferably butyl, 7-alkyl preferably methyl, 8-alkyl preferably methyl, 7-alkoxy preferably 7-methoxy, 8-nitro, 8-amino.

$R_6$

Hydrogen.

The quinaldic acid derivatives according to the invention show promise as therapeutic agents for the treatment of conditions in which combination of an extrinsic antigen with a reaginic antibody is primarily responsible, for example extrinsic asthma, hay fever, urticaria, eczema or atopic dermatitis. Thus the compound of Example 15 which is 4-methoxy-N-(tetrazol-5-yl)-quinaldamide was found to be about 28 times more active than disodium cromoglycate in inhibiting the release of histamine in the peritoneal passive anaphylaxis (PPA) test using the DNP — egg albumen system (J. Exp. Med. (1968), 127, 727).

The invention also provides pharmaceutical compositions which contain a compound of general formula (I) or a salt or ester thereof together with a pharmaceutically acceptable carrier, excipient, or other formulatory agent. The compositions may also contain supplementary medicinal agents, e.g. bronchodilators, antihistamines, tranquillisers, or anxiolytics.

Suitable forms of oral administration include tablets, capsules, syrups or emulsions. For administration by inhalation the compositions according to the invention may be in the form of a powder or snuff or as an aerosol spray presentation. The latter may conveniently be a pressurised pack with a metering valve to deliver a fixed dosage unit or may be an aqueous solution delivered via a nebuliser.

The dosage at which the active ingredient may be administered may vary within a wide range, depending on the age, weight and condition of the patient. A suitable oral range is generally from 20 – 1500 mg and for inhalation is from 1 – 20 mg. The dose may be repeated as required.

The invention also provides a process for the preparation of compounds of formula (I) in which quinaldic acids of general formula (II):

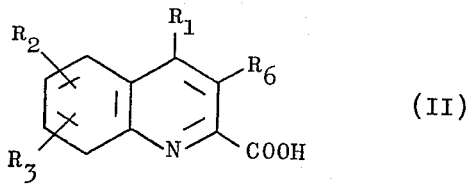

wherein $R_1$, $R_2$, $R_3$ and $R_4$ and $R_6$ have the meanings stated above, are condensed with 5-aminotetrazole. A variety of condensing agents of general application in peptide chemistry may be used to effect this reaction; for example, N,N'-carbonyl diimidazole, N-ethoxycarbonyl-2-ethoxy-1,2-dihydroquinoline, or N,N'-dicyclohexyl carbodiimide in an aprotic solvent such as tetrahydrofuran or dimethylformamide. If necessary heating may be employed. Activated derivatives of the acid (II), e.g. mixed anhydrides or acid halides, may equally be employed. Thus the reaction of the acid halide may be effected in an aprotic medium, such as dioxan or tetrahydrofuran or in an aqueous medium in the presence of an acid acceptor, for example a tertiary organic base such as pyridine or triethylamine or an alkali metal carbonate or bicarbonate such as sodium carbonate or sodium bicarbonate.

The starting acids (II) are either known compounds or they may be prepared by well-established methods of quinoline chemistry. The groups $R_1$–$R_6$ may be present from the start or can be introduced or modified at any stage as required by standard chemical conversions more fully described below and in the Examples.

A particularly useful sequence employs esters of the hydroxy quinaldic acids of general formula (III) wherein $R_2$, $R_3$ and $R_6$ have the meanings given above.

Thus, the ester (III) is converted into the halide (IV), e.g. with $POCl_3$ where Hal is a chlorine atom and the active halogen atom may be displaced with nucleophiles such as amines or alkoxides to give compounds of general formula (V) ($X = NR_4R_5$ or $—OR_4$) wherein $R_2$, $R_3$ and $R_6$ have the meanings stated above and $R_7 =$ Alkyl. These displacement reactions may be effected at elevated temperatures with or without the presence of solvent, e.g. N-methylpyrrolidone, methanol etc. The esters may then be hydrolysed to the acids (V) ($R_7 =$ H), e.g. by warming with aqueous alkali.

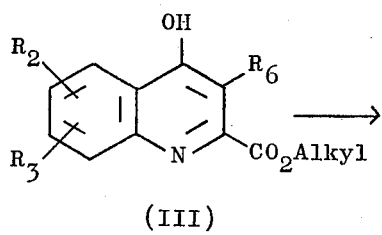

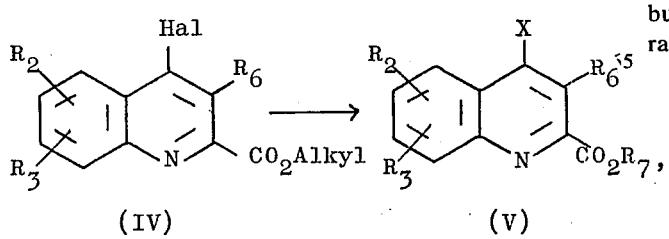

Further examples of transformation of the substituents $R_1$ – $R_6$ of particular utility are the conversions of acids of structure (II), where any of $R_1$, $R_2$ and $R_3$ are hydroxyl groups, into ethers ($—OR_4$) by standard alkylation procedures, e.g. with an alkylating agent $R_4Y$ preferably in a solvent such as 2-butanone or dimethylformamide and in the presence of a base, typically an anhydrous alkali metal carbonate.

Compounds of the invention (I) in which $R_1$ – $R_6$ have specific meanings may also be converted into other compounds of the invention by standard processes. For example, the active halogen atom of (I) ($R_1$ = Hal) may be displaced by amines ($—NR_4R_5$). These displacement reactions maybe effected at elevated temperatures with or without the presence of solvent, e.g. water or methanol. In another reaction the benzyl ether (I) ($R_1 = PhCH_2—O$) may be hydrogenolysed in the presence of a suitable catalyst such as PdO/C to give the amidotetrazole of hydroxyquinaldic acids (I) ($R_1 = HO—$).

The following Examples illustrate the invention:

EXAMPLE 1

N-(1H-Tetrazol-5-yl)quinaldamide

Quinaldic acid (1.1 g) in tetrahydrofuran (50 ml) containing dimethylformamide (5 ml) was treated with a solution of N,N'-carbonyl diimidazole (1 g) in tetrahydrofuran (40 ml) containing dimethylformamide (5 ml). After 3 hours, 5-aminotetrazole (0.65 g) in dimethylformamide (30 ml) was added and the resulting solution was stirred for 2 days at room temperature. The solvent was distilled off under reduced pressure to give an oil which solidified on trituration with water, m.p. 258° (d).

EXAMPLE 2

4-Chloro-N(1H-tetrazol-5-yl)quinaldamide

4-Chloroquinaldic acid (5.7 g) and thionyl chloride (4 ml) in dry benzene (100 ml) were heated under reflux for 2.5 hours. The benzene and the excess of thionyl chloride were distilled off and 4-chloroquinaldoyl chloride, m.p. 104°–106°, was crystallised from cyclohexane.

In a similar manner 4,7-dichloroquinaldoyl chloride, m.p. 120.5° was prepared from 4,7-dichloroquinaldic acid; 6-n butyl-4-chloroquinaldoyl chloride, m.p. 95°–98.5° was prepared from 6-n-butyl-4-chloroquinaldic acid.

5-Aminotetrazole (0.46 g) and triethylamine (0.73 ml) in dry dioxan (25 ml) were stirred and warmed to 35°. 4-Chloroquinaldoyl chloride (1 g) in dioxan (15 ml) was added. The 4-chloro-N(1H-tetrazol-5-yl)quinaldamide was collected, washed with water and dried, m.p. 305° (d).

In a similar manner 6-butyl-4-chloro-N-(1H-tetrazol-5-yl)quinaldamide, m.p. 275° was prepared from 6-butyl-4-chloroquinaldoyl chloride and 5-aminotetrazole.

EXAMPLE 3

4(2-Hydroxyethylamino)-N-(1H-tetrazol-5-yl)quinaldamide

4-Chloro-N(1H-tetrazol-5-yl)quinaldamide (0.8 g), 2-aminoethanol (25 ml) and water (10 ml) were heated at 100° for 3 hours. Aqueous sodium hydroxide (3.5 ml., 2N) and acetone (100 ml) were added and the solid was collected and dissolved in water. The solution was acidified to pH 2 with dilute hydrochloric acid and the solid was filtered off and crystallised from water, m.p. 244° (d).

The sodium salt of 4(2-hydroxyethylamino)-N(1H-tetrazol-5-yl)quinaldamide was prepared as follows:

Aqueous sodium hydroxide (5N) was added dropwise to 4(2-hydroxyethylamino)-N(1H-tetrazol-5-yl)quinaldamide (1 g) in water (20 ml). When the solid had dissolved (pH 10.5) the solution was evaporated under reduced pressure. The residue was dissolved in methanol (20 ml) and the solution was diluted with ethyl acetate (40 ml). The solid which crystallised was collected and dried, m.p. 225°–228°.

EXAMPLE 4

4(3-Hydroxypropylamino)-N(1H-tetrazol-5-yl)quinaldamide

4-Chloro-N(1H-tetrazol-5-yl)quinaldamide (0.5 g), 3-aminopropan-1-ol (10 ml) and water (2 ml) were heated at 100° for 6 hours and cooled. Concentrated hydrochloric acid (13 ml) was added and the solid was collected. A mixture of the solid and water was treated dropwise with 2N sodium hydroxide to give a solution pH 10 and this was treated with glacial acetic acid to give a mixture pH 4. The solid was collected, washed with water and dried, m.p. 244°–245° (d).

EXAMPLE 5

4[(2-Hydroxyethyl)methylamino]-N(1H-tetrazol-5-yl)-quinaldamide, hydrochloride 4-Chloro-N(1H-tetrazol-5-yl)quinaldamide (0.6 g), 2-methylaminoethanol (5 ml) and water (2 ml) were heated on a steam bath for 18 hours and cooled. Hydrochloric acid was added to give a mixture of pH<1 and the solid was filtered off and crystallised from dilute hydrochloric acid, m.p. 205° (d).

In a similar way
4(2,3-Dihydroxypropylamino)-N(1H-tetrazol-5-yl)quinaldamide, hydrochloride, m.p. 264° (d) was prepared from 4-chloro-N(1H-tetrazol-5-yl)quinaldamide (Example 2) and 3-amino-1,2-propanediol.

EXAMPLE 6

4(Morpholino)-N(1H-tetrazol-5-yl)quinaldamide

4-Chloro-N(1H-tetrazol-5-yl)quinaldamide (1 g), morpholine (1.5 g) and water (1.5 ml) were heated on a steam bath for 16 hours. The mixture was acidified with hydrochloric acid and the solid was collected and dissolved in hot aqueous dimethylaminoethanol (20 ml., 5%). Acetic acid (1 ml., glacial) was added and the solid was collected, washed with water and dried, m.p. 88° (d).

In a similar way
4(2-Methoxyethylamino)-N(1H-tetrazol-5-yl)quinaldamide, m.p. 260° (d) was prepared from 2-methoxyethylamine.

EXAMPLE 7

4(2-Aminoethylamino)-N(1H-tetrazol-5-yl)quinaldamide, hydrochloride

4-Chloro-N(1H-tetrazol-5-yl)quinaldamide (1.4 g) and ethylene diamine (6 ml) were heated on a steam bath for 1 hour and cooled. 5N Hydrochloric acid (30 ml) was added. The solid was collected and crystallised from aqueous dimethylformamide, m.p. 252°.

4[(2-Dimethylaminoethyl)methylamino]-N(1H-tetrazol-5-yl)quinaldamide, dihydrochloride, m.p. 126° (d) was prepared similarly from N,N,N'-trimethylethylenediamine and 4-chloro-N(1H-tetrazol-5-yl)quinaldamide.

EXAMPLE 8

4(2-Dimethylaminoethylamino)-N(1H-tetrazol-5-yl)quinaldamide, dihydrochloride 4-Chloro-N(1H-tetrazol-5-yl)quinaldamide (0.3 g), N,N-dimethylethylenediamine (6 ml) and water (2 ml) were heated at 100° for 8 hours. The excess of N,N-dimethylethylenediamine was distilled off under reduced pressure and the residue was treated with aqueous hydrochloric acid to pH 1. The solid, in water (5 ml), was treated with 2N sodium hydroxide to give a solution pH 4. The solid which crystallised from this solution was collected and dried, m.p. 200° (d).

EXAMPLE 9

4-Cyclohexylamino-N(1H-tetrazol-5-yl)quinaldamide, hydrochloride

4-Chloro-N(1H-tetrazol-5-yl)quinaldamide (0.55 g), cyclohexylamine (3 ml) and water (5 ml) were heated on a steam bath for 3 hours and cooled. The solid was collected and dried, m.p. 245° (d).

EXAMPLE 10

4(4-Methylpiperazino)-N(1H-tetrazol-5-yl)quinaldamide, trihydrochloride

4-Chloro-N(1H-tetrazol-5-yl)quinaldamide (0.6 g), N-methylpiperazine (5 ml) and water (1 ml) were heated on a steam bath for 18 hours. Water (5 ml) and dilute hydrochloric acid were added to pH 1 and the solid was collected and washed with 0.1N hydrochloric acid and dried, m.p. 215° (d).

EXAMPLE 11

4-Chloro-6-methoxy-N(1H-tetrazol-5-yl)quinaldamide

N,N'-Carbonyldiimidazole (13.3 g) and 4-chloro-6-methoxyquinaldic acid (19.5 g) in dimethylformamide (100 ml) was stirred at room temperature for 2 hours. 5-Aminotetrazole was added and the mixture was stirred for 16 hours at room temperature. The solution was concentrated to 50 ml. and cooled. The solid was collected and dissolved in a warm mixture of dimethylformamide (50 ml) and dimethylaminoethanol (10 ml). The solid which crystallised was dissolved in water and the solution was acidified to pH 1 with dilute hydrochloric acid. The solid which separated was collected, washed with water and dried, m.p. 300° (d).

EXAMPLE 12

6-Methoxy-4(4-methylpiperazinyl)-N(1H-tetrazol-5-yl)quinaldamide, quinaldamide, hydrochloride 4-Chloro-6-methoxy-N(1H-tetrazol-5-yl)quinaldamide (0.5 g) and N-methylpiperazine (10 g) were heated under reflux for 4 hours. The excess of N-methylpiperazine was distilled off and the residue in water (30 ml) was acidified to pH 2 with dilute hydrochloric acid. The solid was collected, crystallised from water and dried, m.p. 294° (d).

Piperazino-N(1H-tetrazol-5-yl)quinaldamide hydrochloride, m.p. 320° (d), was prepared in a similar way from piperazine and 4-chloro-N(1H-tetrazol-5-yl)quinaldamide.

EXAMPLE 13

4-Chloro-7,8-dimethyl-N(1H-tetrazol-5-yl)quinaldamide

Phosphoryl chloride (25 ml) and 4-hydroxy-7,8-dimethylquinaldic acid, ethyl ester (10 g) were stirred for 16 hours at room temperature. The excess of phosphoryl chloride was distilled off and the oil was treated with ice (200 g). The 4-chloro-7,8-dimethylquinaldic acid, ethyl ester was collected and dried, m.p. 77°–78°.

4-Chloro-7,8-dimethylquinaldic acid, ethyl ester (0.9 g), 2N sodium hydroxide (20 ml) and ethanol (20 ml) heated under reflux for 30 minutes and cooled. The solution was acidified to pH 1 with dilute hydrochloric acid and 4-chloro-7,8-dimethylquinaldic acid was crystallised from aqueous acetic acid and dried, m.p. 165°–166.5°.

In a similar way 6-butyl-4-chloroquinaldic acid, m.p. 119°–121°, was prepared by the hydrolysis of 6-butyl-4-chloroquinaldic acid, ethyl ester.

4-Chloro-7,8-dimethylquinaldic acid (1.72 g) and N,N'-carbonyldiimidazole (1.18 g) in dimethylformamide (15 ml) were stirred for 4 hours at room temperature. 5-Aminotetrazole (1.24 g) was added and the mixture was stirred for 2 days at room temperature. The solid was filtered off and dissolved in a mixture of dimethylformamide and dimethylaminoethanol and the solution was acidified with dilute hydrochloric acid. 4-Chloro-7,8-dimethyl-N(1H-tetrazol-5-yl)quinaldamide was collected, m.p. 262° (d).

EXAMPLE 14

4,7-Dimethoxy-N(1H-tetrazol-5-yl)quinaldamide
4,7-Dimethoxyquinaldic acid

Hydrochloric acid (700 ml, 2N) was added to a stirred mixture of ethyl sodium oxaloacetate (210 g) and benzene (500 ml). The benzene layer was dried over anhydrous magnesium sulphate and filtered. m-Anisidine (130 g) was added to the filtrate and the mixture was heated under reflux for 1 hour, cooled, washed with 2N hydrochloric acid (2 × 250 ml) and with water, dried over anhydrous magnesium sulphate, filtered and evaporated. The residue (235 g) in tetralin (2.3 l.) was heated under reflux for 1 hour and allowed to cool. 4-Hydroxy-7-methoxyquinaldic acid, ethyl ester was collected and was crystallised from methanol and dried, m.p. 218°–219°.

In a similar way 6-butyl-4-hydroxyquinaldic acid, ethyl ester, was prepared from 4-butylaniline and diethyloxaloacetate. 4-Hydroxy-7-methoxyquinaldic acid, ethyl ester (33.5 g) and phosphoryl chloride (70 ml) were heated at 100° for 15 minutes, cooled and poured onto ice (500 g). 4-Chloro-7-methoxyquinaldic acid, ethyl ester was collected, dried and crystallised from light petroleum (b.p. 60°–80°), m.p. 114.5°–116°.

In a similar way 6-butyl-4-chloroquinaldic acid, ethyl ester, m.p. 58.5°–61.5° was prepared from 6-butyl-4-hydroxyquinaldic acid, ethyl ester and phosphoryl chloride.

4-Chloro-7-methoxyquinaldic acid, ethyl ester (7.9 g) was added to a solution of sodium (1.4 g) in dry methanol (40 ml). The mixture was heated under reflux for 2 hours, water (20 ml) was added and heating under reflux was continued for 20 minutes. The mixture was cooled and 4,7-dimethoxyquinaldic acid, sodium salt, was filtered off and crystallised from water. This salt was dissolved in hot water (50 ml) and the solution was acidified with glacial acetic acid. 4,7-Dimethoxyquinaldic acid was collected and dried, m.p. 210.5°–211.5°.

In a similar manner 4,6-Dimethoxyquinaldic acid, m.p. 226.5° (d) was prepared from 4-chloro-6-methoxyquinaldic acid, ethyl ester.

4,7-Dimethoxy-N(1H-tetrazolyl-5-yl)quinaldamide 4,7-Dimethoxyquinaldic acid (3 g) and N,N'-carbonyldiimidazole (2.1 g) in tetrahydrofuran (300 ml) and dimethylformamide (5 ml) were heated under reflux for 30 minutes. 5-Aminotetrazole (1.1 g) in dimethylformamide (6 ml) was added and the mixture was heated under reflux for 30 minutes and cooled. The solid was collected and dissolved in hot dilute sodium hydroxide (20 ml, 2N) and the solution was acidified with glacial acetic acid and cooled. 4,7-Dimethoxy-N(1H-tetrazol-5-yl)quinaldamide was filtered off and dried, m.p. 262°–264°.

EXAMPLE 15

4-Methoxy-N(1H-tetrazol-5-yl)quinaldamide

4-Methoxyquinaldic acid (7.25 g) was dissolved in dry dimethylformamide (20 ml). N,N'-carbonyldiimidazole (5.8 g) was added, and the solution was stirred for 6 hours at room temperature. 5-Aminotetrazole (3.69 g) was added and the mixture was stirred overnight at room temperature. The solid was filtered off, washed with methanol and dissolved in dimethylformamide (500 ml) with the minimum addition of dimethylaminoethanol to effect dissolution. Water (50 ml) was added, and the solution was adjusted to pH 2 by the addition of aqueous hydrochloric acid. The solid was filtered off to give 4-methoxy-N(1H-tetrazol-5-yl)quinaldamide, m.p. 289° (d).

EXAMPLE 15a

4-Methoxy-N(1H-tetrazol-5-yl)quinaldamide, sodium salt

Sodium hydroxide (13.5 ml, 2N) was added to a suspension of 4-methoxy-N(1H-tetrazol-5-yl)quinaldamide (18.05 g) in a mixture of acetone (225 ml) and water (225 ml). The solution which had pH 9.6 was concentrated to a volume of 100 ml. The solid was collected and crystallised from methanol (120 ml) and ethyl acetate (150 ml), m.p. above 300°.

EXAMPLE 16

4-Methoxy-6-nitro-N(1H-tetrazol-5-yl)quinaldamide
4-Hydroxy-6-nitroquinaldic acid, ethyl ester 4-Hydroxyquinaldic acid, ethyl ester (100 g) was nitrated according to the method of W.O. Kermack and A.P. Weatherhead, J. Chem. Soc., 1164, 1940, to give 4-hydroxy-6-nitroquinaldic acid, ethyl ester, m.p. 294°–295°. 4-Hydroxy-8-nitroquinaldic acid, ethyl ester, m.p. 191°–192°, was also formed and was isolated on crystallisation of the mixture from ethyl acetate and concentration of the mother liquors.

4-Chloro-6-nitroquinaldic acid, ethyl ester

4-Hydroxy-6-nitroquinaldic acid, ethyl ester (39.5 g) and phosphoryl chloride (80 ml) were heated for 15 minutes on a steam bath. The excess of phosphoryl chloride was distilled off, the residue was treated with toluene (200 ml) and 4-chloro-6-nitroquinaldic acid, ethyl ester, m.p. 165°–166°, was filtered off.

In a similar way
 4-Chloro-8-nitroquinaldic acid, ethyl ester, m.p. 118°–119° was prepared from 4-hydroxy-8-nitroquinaldic acid, ethyl ester.

4-Methoxy-6-nitroquinaldic acid, ethyl ester

4-Chloro-6-nitroquinaldic acid, ethyl ester (29.6 g) was added to a solution of sodium (6 g) in dry methanol and the mixture was stirred and heated under reflux for 3 hours. Water (200 ml) was added and the mixture was boiled for 5 minutes, cooled and acidified to pH 2 with 5N hydrochloric acid, 4-Methoxy-6-nitroquinaldic acid was filtered off and crystallised from a mixture of methanol and dimethylformamide, m.p. 219°.

4-Methoxy-8-nitroquinaldic acid, m.p. above 400° was prepared in a similar way from 4-chloro-8-nitroquinaldic acid, ethyl ester.

4-Methoxy-6-nitro-N(1H-tetrazol-5-yl)quinaldamide

4-Methoxy-6-nitroquinaldic acid (1 g) and N,N'-carbonyldiimidazole (0.7 g) in dimethylformamide (25 ml) were heated on a steam bath for 1 hour. 5-Aminotetrazole (0.7 g) was added and the mixture was heated for 30 minutes on a steam bath. 4-Methoxy-6-nitro-N(1H-tetrazol-5-yl)quinaldamide, m.p. 308° was filtered off.

EXAMPLE 17

4-Methoxy-8-nitro-N(1H-tetrazol-5-yl)quinaldamide

4-Methoxy-8-nitroquinaldic acid (3.6 g) (see Example 16) and N,N'-carbonyldiimidazole (2.5 g) in dimethylformamide (70 ml) were heated on a steam bath for 1 hour. 5-Aminotetrazole (2.5 g) was added and the mixture was heated on a steam bath for 1 hour and cooled. 4-Methoxy-8-nitro-N(1H-tetrazol-5-yl)quinaldamide, compound with imidazole, m.p. 238°, was filtered off and was triturated with 2N hydrochloric acid (50 ml). 4-Methoxy-8-nitro-N(1H-tetrazol-5-yl)quinaldamide was collected and dried, m.p. 268° (d).

EXAMPLE 18

6-Amino-4-methoxy-N(1H-tetrazol-5-yl)quinaldamide

4-Methoxy-6-nitro-N(1H-tetrazol-5-yl)quinaldamide (1 g), 2-dimethylaminoethanol (1 ml) and 10% palladium on charcoal (0.1 g) in water (25 ml) were shaken with hydrogen at room temperature and atmospheric pressure for 22 hours. The catalyst was filtered off and the filtrate was evaporated. The residue was triturated with methanol and the solid was collected, m.p. 286°–287° (d).

In a similar way,
 8-Amino-4-methoxy-N(1H-tetrazol-5-yl)quinaldamide, m.p. 276° (d), was prepared by the hydrogenation of 4-methoxy-8-nitro-N(1H-tetrazol-5-yl)quinaldamide.

EXAMPLE 19

4-Allyloxy-N(1H-tetrazol-5-yl)quinaldamide

4-Hydroxyquinaldic acid, ethyl ester (16 g), allyl bromide (22.5 g) and anhydrous potassium carbonate (30 g) in dimethylformamide (300 ml) were stirred and heated on a steam bath for 20 hours. The mixture was filtered, the filtrate was evaporated and the residue was crystallised from a mixture of ethyl acetate and light petroleum (b.p. 60°–80°) to give 4-allyloxyquinaldic acid, ethyl ester.

4-Allyloxyquinaldic acid, ethyl ester (2 g), 2N sodium hydroxide (20 ml) and ethanol (10 ml) were heated on a steam bath for 45 minutes. The hot solution was treated with glacial acetic acid (3 ml) and the solution was cooled. 4-Allyloxyquinaldic acid was collected, washed with water and dried, m.p. 155°–155.5°.

N,N'-Carbonyldiimidazole (1.27 g) and 4-allyloxyquinaldic acid (1.2 g) in dimethylformamide (30 ml) were heated at 100° for 4 hours. 5-Aminotetrazole (1.33 g) was added and the mixture was stirred at 100° for 1 hour and cooled. Water (30 ml) was added and the solid was collected and dissolved in hot aqueous dimethylaminoethanol (15 ml, 5%). The solution was filtered and the filtrate was acidified with glacial acetic acid. 4-Allyloxy-N(1H-tetrazol-5-yl)quinaldamide was collected and dried, m.p. 260° (d).

EXAMPLE 20

4(2-Formyloxyethoxy)-N(1H-tetrazol-5-yl)quinaldamide

4-Hydroxyquinaldic acid, ethyl ester (1 g), 2-bromoethanol (2 g) and anhydrous potassium carbonate (10 g) in butan-2-one (50 ml) were stirred and heated under reflux for 6 hours. The solid was filtered off, and the filtrate was evaporated. The residue was triturated with ethyl acetate and 4(2-hydroxyethoxy)quinaldic acid, ethyl ester was crystallised from ethyl acetate, and dried, m.p. 146.5°–148°.

4(2-Hydroxyethoxy)quinaldic acid, ethyl ester (4 g) and 2N sodium hydroxide (25 ml) were warmed to 60° for 10 minutes. The solution was acidified to pH 1 with dilute hydrochloric acid and 4(2-hydroxyethoxy)quinaldic acid was collected and crystallised from aqueous dimethyl sulphoxide, and dried, m.p. 226° (d).

Formic acid (9 ml) was added to acetic anhydride (18 ml) which was cooled to below 5°. The solution was warmed to 50° for 15 minutes, cooled to below 5° and added to 4(2-hydroxyethoxy)quinaldic acid (2.05 g) in a mixture of dimethylformamide (100 ml), dimethylsulphoxide (20 ml) and pyridine (20 ml) also cooled to 5°. The solution was stirred at room temperature for 16 hours and concentrated. 4(2-Formyloxyethoxy)quinaldic acid was collected, washed with ether and dried, m.p. 199° (d).

N,N'-Carbonyldiimidazole (1.55 g) was added to 4(2-formyloxyethoxy)quinaldic acid (2.5 g) in hot tetrahydrofuran (200 ml) and the solution was heated under reflux for 1.5 hours. 5-Aminotetrazole (0.85 g) in dimethylformamide (4 ml) was added and the mixture was heated under reflux for 2.5 hours. 4(2-Formyloxyethoxy)-N(1H-tetrazol-5-yl)quinaldamide was filtered off and dried, m.p. 263°.

EXAMPLE 21

4-(2-Hydroxyethoxy)-N(1H-tetrazol-5-yl)quinaldamide

4(2-Formyloxyethoxy)-N(1H-tetrazol-5-yl)quinaldamide (2 g) in water (100 ml) and 2N sodium hydroxide (14 ml) was warmed on a steam bath for 15 minutes, and cooled. The solution was acidified to pH 2 with dilute hydrochloric acid. The solid was collected, crystallised from aqueous dimethylformamide and dried, m.p. 261.5°–262° (d).

EXAMPLE 22

4-Benzyloxy-N(1H-tetrazol-5-yl)quinaldamide

4-Benzyloxyquinaldic acid (2.8 g), 5-aminotetrazole (1 g) and N-ethoxycarbonyl-2-ethoxy-1,2-dihydroquinoline (EEDQ) (2.5 g) in dimethylformamide (20 ml) were stirred at room temperature for 6 hours. The solid in dimethylformamide (20 ml) was treated dropwise with dimethylaminoethanol and the solution was filtered, diluted with water (200 ml) and acidified with 2N hydrochloric acid to give a solid, m.p. 302° (d).

EXAMPLE 23

4-Hydroxy-N(1H-tetrazol-5-yl)quinaldamide

4-Benzyloxy-N(1H-tetrazol-5-yl)quinaldamide (1.5 g) and dimethylaminoethanol (0.5 ml) in dimethylformamide (20 ml) were shaken with hydrogen at atmospheric pressure and room temperature in the presence of 10% palladium on charcoal catalyst (0.15 g). When uptake of hydrogen had ceased, the catalyst was filtered off and the filtrate was evaporated. The residue was dissolved in water (50 ml) and the solution was acidified with dilute hydrochloric acid. The solid was collected, and crystallised from aqueous dimethylformamide and dried, m.p. 281° (d).

EXAMPLE 24

4-Butyloxy-N(1H-tetrazol-5-yl)quinaldamide

Sodium (0.92 g) was dissolved in butanol (50 ml) and 4-chloroquinaldic acid, ethyl ester (4.7 g) was added. The mixture was heated under reflux for 1 hour. Water (50 ml) was added and the mixture heated under reflux for 1 hour and concentrated to a volume of 20 ml. The sodium salt of the required acid crystallised and was collected and dissolved in warm water (50 ml). The solution was acidified to pH 2 with dilute hydrochloric acid and 4-butyloxyquinaldic acid was collected and dried, m.p. 151.5°–153° (d).

4-Butyloxyquinaldic acid (0.83 g) in dry dimethylformamide (25 ml) was treated with N,N'-carbonyldiimidazole (0.55 g) and the mixture stirred at 60° for 3 hours. 5-Aminotetrazole (0.35 g) was added and the solution kept 72 hours and evaporated to a volume of 5 ml. Dilute hydrochloric acid was added and the 4-butyloxy-N(1H-tetrazol-5-yl)quinaldamide formed was crystallised from aqueous dimethylformamide, m.p. 282° (d).

In a similar manner 4,6-Dimethoxyquinaldic acid (Example 14) was converted to 4,6-dimethoxy-N(1H-tetrazol-5-yl)quinaldamide, m.p. 280° (d).

EXAMPLe 25

4-(2-Methoxyethoxy)-N(1H-tetrazol-5-yl)quinaldamide

4-Chloroquinaldic acid, ethyl ester (6 g) was added to a solution of sodium (1.3 g) in 2-methoxyethanol (50 ml). The mixture was stirred and heated at 90° for 1 hour. Water (20 ml) was added and the mixture was heated at 90°–95° for 15 minutes and evaporated. 4-(2-Methoxyethoxy)quinaldic acid was crystallised from a mixture of glacial acetic acid and ether, and dried, m.p. 195°–196.5° (d). 4(2-Methoxyethoxy)quinaldic acid (1.0 g) and N,N'-carbonyldiimidazole (0.72 g) in tetrahydrofuran (50 ml) were heated under reflux for 17 hours. 5-Amino-1H-tetrazole (0.45 g) was added and the mixture was heated under reflux for 2 hours. The solid was dissolved in aqueous dimethylaminoethanol (25 ml., 5%) and the solution was filtered and acidified with glacial acetic acid. 4(2-Methoxyethoxy)-N(1H-tetrazol-5-yl)quinaldamide, was filtered off and dried, m.p. 275°–276.5° (d).

EXAMPLE 26

4-Ethylamino-N(1H-tetrazol-5-yl)quinaldamide

4-Chloro-N(1H-tetrazol-5-yl)quinaldamide (1 g) and aqueous ethylamine (20 ml., 70% w/w) were heated to 100° in an autoclave for 10 hours. The mixture was evaporated, the residue was dissolved in water (10 ml) and the solution was acidified with hydrochloric acid to pH 1. The solid was collected and dissolved in aqueous dimethylaminoethanol (20 ml., 5%) and the solution was warmed to 60° and acidified with dilute hydrochloric acid. 4-Ethylamino-N(1H-tetrazol-5-yl)quinaldamide was collected and dried, m.p. 237° (d).

EXAMPLE 27

Inhalation aerosol

A formula for an inhalation aerosol is given below. The quantities given are those contained in a metered dose containing 2 mg of active ingredient. The active ingredient is the sodium salt of the compound of Example 15. This may be replaced by any one of the other compounds according to the invention specifically described herein.

Formula

| | |
|---|---|
| Active ingredient Sodium salt (hemihydrate) | 2.25 mg |
| Emulsifier YN | 0.075 mg |
| Propellant Arcton 11 | 23.10 mg |
| Propellant Arcton 12 | 59.30 mg |

Method

The active ingredient Sodium salt is micronised and mixed with the propellant 11 together with the Emulsifier YN. The required quantity of this suspension is filled into an aerosol can and a suitable metering valve crimped in place. The propellant 12 is filled into the can through the valve.

Emulsifier YN is supplied by Cadbury Brothers Ltd., Bournville, England.

Propellant 11 is Arcton 11 supplied by Imperial Chemical Industries Limited.

We claim:
1. A compound of the formula:

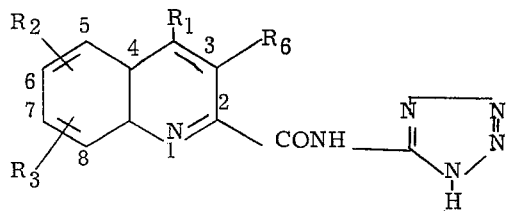

in which $R_1$, $R_2$ and $R_3$ independently represent a hydrogen atom, alkyl, nitro, a halogen atom or $-NR_4R_5$ or $-OR_4$; in which $R_4$ and $R_5$ independently represent a hydrogen atom, alkenyl, cycloalkyl, alkyl, or alkyl substituted by alkoxy, hydroxy, amino, alkylamino, dialkylamino or phenyl and $R_6$ represents a hydrogen atom or a pharmaceutically acceptable ester thereof with a simple aliphatic acid; or a pharmaceutically acceptable salt thereof, any alkyl moiety being of 1 to 6 carbon atoms, any alkenyl moiety being of 2 to 6 carbon atoms, any cycloalkyl moiety being of 5 or 6 carbon atoms, $R_2$ and $R_3$, when both are vicinal and other than hydrogen, said substituents are methyl and there being present no more than one nitro substituent.

2. A compound as claimed in claim 1 in which the group $R_1$ is hydrogen, halogen, hydroxy, alkylamino, hydroxyalkylamino, hydroxyalkyl-alkylamino, dihydroxyalkylamino, alkoxyalkylamino, aminoalkylamino, dialkylaminoalkylalkylamino, cycloalkylamino, alkoxy, alkenyloxy, aralkyloxy, hydroxyalkoxy,- 2-formyloxyethoxy, or alkoxyalkoxy.

3. A compound as claimed in claim 1 in which at least one of the groups $R_2$ and $R_3$ is hydrogen, 6-alkoxy, 6-nitro, 6-amino, 6-alkyl, 7-alkyl 8-alkyl, 7-alkoxy, 8-nitro or 8-amino.

4. A compound as claimed in claim 1 in which $R_6$ is hydrogen.

5. The compound of claim 1 which is N-(1H-Tetrazol-5-yl)quinaldamide.

6. The compound of claim 1 which is 4-Chloro-(1H-tetrazol-5-yl)quinaldamide.

7. The compound of claim 1 which is 6-Butyl-4-chloro-N(1H-tetrazol-5-yl)quinaldamide.

8. The compound of claim 1 which is 4(2-Hydroxyethylamino)-N(1H-tetrazol-5-yl)quinaldamide.

9. The compound of claim 1 which is the sodium salt of the compound of claim 7.

10. The compound of claim 1 which is 4(3-Hydroxypropylamino)-N(1H-tetrazol-5-yl)quinaldamide.

11. The compound of claim 1 which is 4[(2-Hydroxyethyl)methylamino]-N(1H-tetrazol-5-yl)quinaldamide, hydrochloride.

12. The compound of claim 1 which is 4(2,3-Dihydroxypropylamino)-N(1H-tetrazol-5-yl)quinaldamide, hydrochloride.

13. The compound of claim 1 which is 4(2-Methoxyethylamino)-N(1H-tetrazol-5-yl)quinaldamide.

14. The compound of claim 1 which is 4(2-Aminoethylamino)-N(1H-tetrazol-5-yl)quinaldamide, hydrochloride.

15. The compound of claim 1 which is 4[(2-Dimethylaminoethyl)methylamino]-N(1H-tetrazol-5-yl)quinaldamide, dihydrochloride.

16. The compound of claim 1 which is 4(2-Dimethylaminoethylamino)-N(1H-tetrazol-5-yl)quinaldamide, dihydrochloride.

17. The compound of claim 1 which is 4-Cyclohexylamino-N(1H-tetrazol-5-yl)quinaldamide, hydrochloride.

18. The compound of claim 1 which is 4-Chloro-6-methoxy-N(1H-tetrazol-5-yl)quinaldamide.

19. The compound of claim 1 which is 4-Chloro-7,8-dimethyl-N(1H-tetrazol-5-yl)quinaldamide.

20. The compound of claim 1 which is 4,7-Dimethoxy-N(1H-tetrazol-5-yl)quinaldamide.

21. The compound of claim 1 which is 4-Methoxy-N(1H-tetrazol-5yl)quinaldamide.

22. The compound of claim 1 which is 4-Methoxy-N(1H-tetrazol-5-yl)quinaldamide, sodium salt.

23. The compound of claim 1 which is 4-Methoxy-6-nitro-N(1H-tetrazol-5-yl)quinaldamide.

24. The compound of claim 1 which is 4-Methoxy-8-nitro-N(1H-tetrazol-5-yl)quinaldamide.

25. The compound of claim 1 which is 6-Amino-4-methoxy-N(1H-tetrazol-5-yl)quinaldamide.

26. The compound of claim 1 which is 8-Amino-4-methoxy-N(1H-tetrazol-5-yl)quinaldamide.

27. The compound of claim 1 which is 4-Allyloxy-N(1H-tetrazol-5-yl)quinaldamide.

28. The compound of claim 1 which is 4(2-Formyloxyethoxy)-N(1H-tetrazol-5-yl)quinaldamide.

29. The compound of claim 1 which is 4(2-Hydroxyethoxy)-N(1H-tetrazol-5-yl)quinaldamide.

30. The compound of claim 1 which is 4-Benzyloxy-N(1H-tetrazol-5-yl)quinaldamide.

31. The compound of claim 1 which is 4-Hydroxy-N(1H-tetrazol-5-yl)quinaldamide.

32. The compound of claim 1 which is 4-Butyloxy-N(1H-tetrazol-5-yl)quinaldamide.

33. The compound of claim 1 which is 4,6-dimethoxy-N(1H-tetrazol-5-yl)quinaldamide.

34. The compound of claim 1 which is 4-(2-Methoxyethoxy)-N(1H-tetrazol-5-yl)quinaldamide.

35. The compound of claim 1 which is 4-Ethylamino-N(1H-tetrazol-5-yl)quinaldamide.

* * * * *

UNITED STATES PATENT OFFICE
CERTIFICATE OF CORRECTION

Patent No. 3,932,416         Dated January 13, 1976

Inventor(s) David Edmund BAYS et al

It is certified that error appears in the above-identified patent and that said Letters Patent are hereby corrected as shown below:

In the claims, correct the formula between lines 5 and 15 of column 13, as follows:

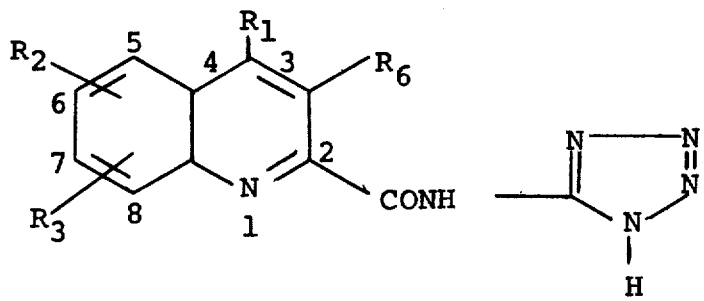

Column 13, line 22, after "atom" insert --or alkyl; --.

Signed and Sealed this sixteenth Day of August 1977

[SEAL]

Attest:

RUTH C. MASON
Attesting Officer

C. MARSHALL DANN
Commissioner of Patents and Trademarks